United States Patent [19]
Lahtinen et al.

[11] Patent Number: 5,130,469
[45] Date of Patent: Jul. 14, 1992

[54] DERIVATIVES OF N,N-BIS(2,2-DIMETHYL-2-CARBOXY-ETHYL)AMINE, MANUFACTURING PROCEDURE AND USE OF SAME

[75] Inventors: Leila Lahtinen, Helsinki; Oili Riutta, Hyvinkää; Pirkko Vohlonen, Helsinki; Ulf Nummelin, Porvoo, all of Finland; Kjell Ankner, Mölnlycke, Sweden; Eija Valtonen; Soile Himanen, both of Porvoo, Finland

[73] Assignee: Neste Oy, Finland

[21] Appl. No.: 566,401

[22] PCT Filed: Jan. 12, 1990

[86] PCT No.: PCT/FI90/00013

§ 371 Date: Aug. 15, 1990

§ 102(e) Date: Aug. 15, 1990

[87] PCT Pub. No.: WO90/08129

PCT Pub. Date: Jul. 26, 1990

[30] Foreign Application Priority Data

Jan. 13, 1989 [FI] Finland .................. 890171

[51] Int. Cl.$^5$ ............................ C07C 229/26
[52] U.S. Cl. ............................ 500/171; 560/44
[58] Field of Search ........... 560/171, 44; 562/571, 562/526; 564/471

[56] References Cited

U.S. PATENT DOCUMENTS

| | | | |
|---|---|---|---|
| 2,179,215 | 11/1939 | Jacobson | 564/471 |
| 2,267,277 | 12/1941 | Houk et al. | 564/471 |
| 2,394,230 | 2/1946 | Billman | 562/526 |
| 2,781,390 | 2/1957 | Manheimer | 562/571 |
| 2,790,778 | 4/1957 | Spivack et al. | 252/392 |
| 3,515,754 | 6/1970 | Mod et al. | 560/171 |
| 4,146,735 | 3/1976 | Carpenter et al. | 562/526 |
| 4,533,500 | 8/1985 | Chauvin et al. | 560/171 |

FOREIGN PATENT DOCUMENTS

| | | | |
|---|---|---|---|
| 1150313 | 7/1983 | Canada | 564/471 |
| 2748208 | 5/1978 | Fed. Rep. of Germany | 560/171 |

*Primary Examiner*—James H. Reamer
*Attorney, Agent, or Firm*—Steinberg & Raskin

[57] ABSTRACT

The present invention concerns N-acyl or N-alkyl derivatives of N,N-bis(2,2-dimethyl-2-carboxyethyl)amine

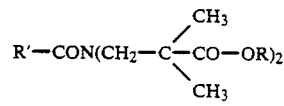

or

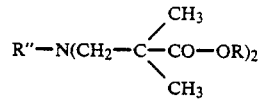

in which R and R'' are similar or different $C_1$-$C_{10}$-alkyl or aryl groups, R'' is a $C_3$-$C_{12}$-alkyl or aralkyl group which may contain an ester group in the carbon chain. Said derivatives are prepared by condensing ammonium halide or ammonium sulphate, formaldehyde and isobutyraldehyde, by oxidizing the condensation product thus obtained into acid form, by esterifying, and finally, by N-acylating or N-alkylating. The obtained compounds can be used for plasticizing, stabilizing, lubricating and anticorrosive agents, and for metal complexing agent for polymers, in particular polymers and polymer mixtures of vinyl chloride.

14 Claims, No Drawings

DERIVATIVES OF N,N-BIS(2,2-DIMETHYL-2-CARBOXY-ETHYL)AMINE, MANUFACTURING PROCEDURE AND USE OF SAME

The present invention concerns new N-alkyl or N-acyl derivatives of N,N-bis (2,2-dimethyl-2-carboxyethyl), the manufacturing procedure and utilization of the same.

The formula of the new compounds of the invention is as follows.

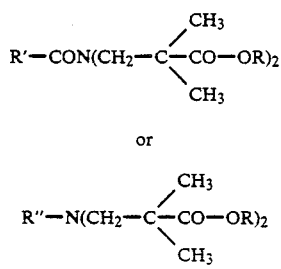

or

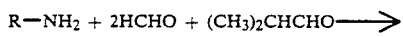

wherein R and R'' are similar or different $C_1$–$C_{10}$-alkyl or -aryl groups, R' is a $C_3$–$C_{12}$-alkyl or an aralkyl group which may contain a carboxyl ester group in the carbon chain.

It is known in the art that the primary and secondary amines react with formaldehyde and isobutylaldehyde (cf. EP No. 46288 and Arch. Pharmaz. 308/75, p. 352), producing either direct-chain or cyclic Mannich reaction products (formulae 1 and 2).

$$R-NH_2 + 2HCHO + (CH_3)_2CHCHO \longrightarrow \quad (1)$$

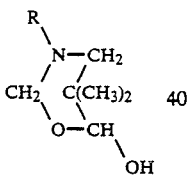

$$R_2NH + HCHO + (CH_3)_2CHCHO \longrightarrow \quad (2)$$

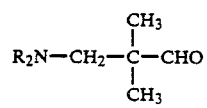

In the present invention, the modified Mannich reaction is used as an intermediate step in the preparation of different N-alkyl- and N-acyl-derivatives of N,N-bis(2,2-dimethyl-2-carboxyethyl)amine in accordance with the following reaction formula (3–7).

$$NH_4Y + 2 HCHO + 2(CH_3)_2CHCHO \longrightarrow \quad (3)$$

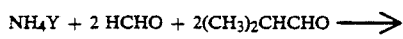

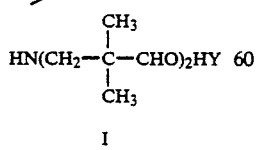

This condensation reaction (3) in which the group Y may be halide or sulphate can be accomplished at 50° to 90° C. in about three hours, either under refluxing conditions or under small overpressure using paraformaldehyde, trioxane or 40% of aqueous formaldehyde solution for starting material.

Thereafter, the obtained compound is oxidized as taught by formula (4):

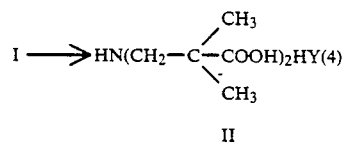

The oxidation reaction (4) can be performed using conventional oxidation procedures such as oxygen, ozone, peroxide, hypohalogen acids, permanganate, chromate, or dichromate oxidation. A particularly advantageous oxidation procedure is e.g. oxidation with about 50% hydrogen peroxide, which takes about three hours at 50° to 75° C.

The oxidized product is esterified according to the reaction (5):

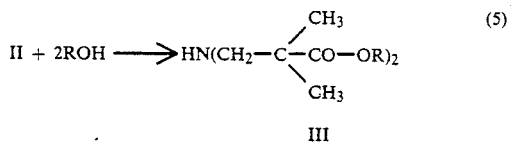

The esterification of the compound II can be accomplished using a number of conventional esterification procedure with organic or mineral acids (p-toluene sulphonic acid, HCl, etc.) as catalyst. It is particularly advantageous to use gaseous hydrochloric acid, and the reaction is accomplished at 100° to 150° C., with reaction times from about three to six hours.

Thereafter, the esterified product is acylated (formula 6) or alkylated (7).

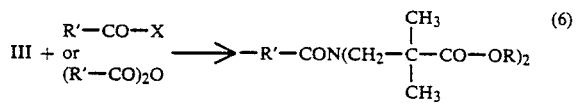

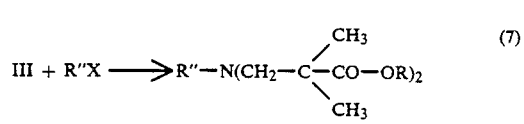

In the formulae 1–7, R and R' refer to a similar or different alkyl or aryl group with 1–12 carbon atoms, and R'' refers to an alkyl or aryl group or a group which in addition to the hydrocarbon chain contains a COOR group. X refers to halogen.

The N acylation of the compound III can be performed using advantageous acid halide or anhydride. More advantageous is acylation with acid chloride at 20° to 100° C. for 2 to 20 hours.

The N alkylation of the compound III can be performed e.g. using the ester of 2-chloroacetic acid at 140° to 150° C. for 3 to 8 hours.

The compounds of type IV and V concerned in the present invention are therefore new in chemical composition, manufacturing process and applications. Their manufacture and testing in particular for uses as PVC plasticizers and stabilization are described more in detail in the following examples.

EXAMPLE 1

Item A

In a reactor, which was equipped with a mixer, a reflux condenser and a thermometer, 66.9 g ammonium chloride, 162 g formaline and 144 g isobutyraldehyde and 1 ml hydrochloric acid were charged. The mixture was heated up to 60° C., whereby the isobutyraldehyde started to reflux. At the end of the refluxing the temperature was raised to 80° C. at which the boiling was continued for 2.5 hrs. The condensation product (362 g) thus obtained was dissolved in acetic acid and heated to 60° C., whereafter 158.1 g 47% hydrogen peroxide was added during one hour. After the addition, the mixture was boiled for 2 hours at 70° to 75° C. The water was evaporated from the reaction mixture, and the raw product thus obtained was recrystallized from the acetic acid-ethyl acetate mixture. The crystallized product was filtered and washed with ethyl methyl ketone-toluene mixture and petroleum ether. The melting point of the hydrochloride salt of the iminodiacid II was from 175° to 179° C. and the yield was 145.3 g (57.3% of the theoretical yield based on the quantity of the isobutanol used; 13CNMR/ppm; 21.9; 39.7, 55.8 and 178.7).

Item B

The hydrochloride salt of iminodiacid II (101.5 g), 2-ethylhexanol (220 g) and toluene (150 ml) were charged in a reactor equipped with a Dean & Stark water separation apparatus and equipment for feeding the hydrogen chloride gas. The mixture was boiled at the boiling point of toluene for about 6 to 7 hrs, or until all water formed in the reaction had distilled over into the water separation apparatus as an azeotropic mixture with toluene. Hydrogen chloride gas was bubbled (feeded) slowly during the whole reaction. Ether was added into the reaction mixture and the organic phase thus obtained was washed with diluted NaOH solution and water. The solvents and the excess of alcohol were distilled off. The product, the di(2-ethylhexyl)-ester of iminodiacid, (III, R is 2-ethylhexyl), was distilled at vacuum, the b. p. being 150° to 160° C. per 0.3 m bar. The yield was 115 g (65.2% from the theoretical quantity) and the purity of the product was 98% (GC). Identification 13CNMR/ppm: 11.1–39.9 (2×9C), 43.9 (2×quaternary C), 59.5 (2×N—CH$_2$), 66.6 (2×—O—CH$^2$), 177.4 (2×C=O).

Item C 22 g di(2-ethylhexyl)ester of iminodiacid III and 4.3 g pyridine were dissolved in dry diethyl ether. N-octanoyl, 8.5 g n-octanoyl chloride dissolved in dry ether was added into the mixture. The reaction mixture was refluxed at the boiling point of the ether for 3 hours. The product mixture was washed with diluted hydrochloric acid, with diluted NaOH solution and, finally, until the waistings are neutral, with water are neutral. The raw product (27.0 g) obtained after the evaporation of the solvent neutral contained 90% of N-acylated product IV in which R was 2-ethylhexyl and R' n-heptyl. Identification: 13 CNMR/ppm: 11.1–39.1. (25C), 43.9 & 44.3 (2×quaternary C), 53.4 & 55.8 (2×N—CH$_2$—), 67.1 & 67.5 (2×—O—CH$_2$—), 174.8 & 176.7 & 177.2 (3×C=O).

EXAMPLE 2

The reaction performed in Item C of Example 1 was repeated, but instead of the n-octanoyl chloride, 8.5 g 2-ethylhexanoylchloride was used. The reaction mixture was refluxed for 5 hours at the boiling point of the ether and thereafter, it was mixed for further 20 hrs at room temperature. The reaction mixture was washed and treated as presented in Example 1/C.

The raw product (26.4 g) contained 87% of the acylated product IV in which R was 2-ethylhexyl and R' 1-ethyl pentyl. Identification: 13CNMR/ppm: 11.0–38.9 (24C), 42.6 (CHCON), 43.8 (2×quaternary C), 52.9 & 55.0 (2×N—CH$_2$), 66.9 & 67.4 (2×—O—CH$_2$), 176.0 & 177.0 & 177.9 (3×C=O).

EXAMPLE 3

The reaction presented in Item C of Example 1 was repeated, but 4.2 g of acetyl chloride was used as an acid chloride. The liquid raw product (22.1 g) thus obtained contain 95% of the acetylated product IV (R was 2-ethylhexyl), R' was methyl). Identification: 13CNMR/ppm: 11.8–38.8 (19C), 43.7 & 44.3 (2×quaternary C.), 53.4 & 56.9 (2×N—CH$_2$—), 67.1 & 67.4 (—O—CH$_2$—), 171.9 & 176.6 & 176.9 (3×C=O).

EXAMPLE 4

22 g di(2-ethylexhyl)ester of iminodiacid III produced as in Item B of Example 1 and 4.3 g pyridine was dissolved in dry ether. 5.3 g of acetic acid anhydride was added in the mixture at room temperature, whereafter the reaction mixture was made to be refluxed at the boiling point of the ether for 5 hours. The reaction mixture was washed and treated further as presented in Item 1/C. The raw product thus obtained contained 27% of acetylated diester IV (R was 2ethylhexyl, R' was methyl) and 72% of unreacted starting material.

EXAMPLE 5

The N-benzoyl derivative of the di(2-ethylhexyl)ester of iminodiacid was prepared in the manner described in Example 3, with the exception that the acetyl chloride was substituted by 7.3 g of benzoylchloride. The yield of the yellowish oily raw product was 26 g containing 23.9 g of the desired product.

Identification: 13CNMR/ppm: 10.9–38.8 (18C), 44.4 (2×quaternary C), 52.8 & 58.1 (2×N—CH$_2$—), 67.4 (2×—O—CH$_2$—), 127.8 & 128.4 & 128.9 & 136.7 (2+2+2+1 arom. C), 173.8 & 176.6 (3×C=O).

EXAMPLE 6

The di(2-ethylhexyl)-ester III of iminodiacid (22 g) obtained as described in Item B of Example 1 was cooled to 0° C., whereafter 36 g of 10% NaOH solution were added. During about 15 min 8.5 g of benzoyl chloride was added at such a rate that the temperature did not rise above 0° C. After the addition, the mixing was continued at 0° C. for 0.5 hour, whereafter the reaction mixture was allowed to warm up slowly to room temperature. Finally, the reaction mixture was extracted in ether and the organic phase was washed with water. The solvent was evaporated. The raw product contained 77% of benzoylated diester IV in which R was thus 2-ethylhexyl and R' was phenyl. In addition, 22% of unreacted starting material was analyzed from the raw product.

EXAMPLE 7

2 g of di(2-ethylhexyl)ester of iminodiacid III, produced as in Item B of Example 1, and 8.8 g ethyl chloro acetate were refluxed in nitrogen atmosphere for 5.5 hours, whereafter the excess of ethyl chloro acetate was distilled off as an of azeotropic mixture with xylene. According to the gas chromatograph, 35% of the diester of iminodiacid had reacted into an N-ethyoxycarbonyl methyl-substituted product V (R was 2-ethylhexyl, R" ethoxycarbonyl methyl). Identification: MS spectrum: m/e 528 (M+1), 454, 328, 216, 116, 57.

EXAMPLE 8

Item A

As in Item B of Example 1, dioctyl ester of iminodiacid III (R was n-octyl) was prepared by using 220 g of n-octanol of 2-ethylhexanol as the starting material. The product was distilled at vacuum, the b. p. 200° to 210° C./2.0 mbar. The yield was 154.4 g (68% from the theoretical quantity).

Item B

An N-octanoyl derivative of dioctyl ester of iminodiacid IV (R=N-octyl and R'=n-heptyl) was prepared as in Item C of Example 1 starting with the product obtained in the manner described in Item A of Example 8 and with n-octanoyl chloride. The yield and the purity of the product were equivalent to the yield in Item C of Example 1. Identification: GC: m/e 568 (M+1).

EXAMPLES 9-11

From the dioctyl ester of iminodiacid (22 g) obtained as described in item A of Example 8 N-2-ethylhexanoyl derivative, N-acetyl derivative and N-benzoyl derivative were prepared as in Examples 2-3 and 5. The products are oily and are produced with yields of 85 to 91%.
Identification: Compound IV in which
R was n-octyl and R' 1-ethylpentyl: m/e 568 (M+1)
R was n-octyl and R' methyl: m/e 484 (M+1)
R was n-octyl and R' phenyl: m/e 546 (M+1)

The results of the N-acylated or N-alkylated derivatives IV or V of iminodiacid diesters III described as in the above Example 1/C - 7 and 8/B -11 are shown in Table 1.

TABLE 1

| Example | Starting material III in which R is | Catalyst/ R'CO and R"X | Product IV/V in which R'/R" is | Yield/ % |
|---|---|---|---|---|
| 1C | 2-ethylhexyl | pyridine/ R' = n-heptyl X = Cl | IV, R' = n-heptyl | 86 |
| 2 | 2-ethylhexyl | pyridine/ R' = 1-ethyl-pentyl X = Cl | IV, R' = 1-ethylpentyl | 84 |
| 3 | 2-ethyl-hexyl | pyridine/ R' = methyl X = Cl | IV, R' = methyl | 87 |
| 4 | 2-ethyl-hexyl | pyridine/ R' = methyl X = Cl | IV, R' = methyl | 27 |
| 5 | 2-ethyl-hexyl | pyridine/ R' = phenyl X = Cl | IV, R' = phenyl | 89 |
| 6 | 2-ethyl-hexyl | NaOH/ R' = phenyl X = Cl | IV, R' = phenyl | 72 |
| 7 | 2-ethyl-hexyl | — R" = ethyl-acetyl X = Cl | V, R" = ethyl-acetyl | 35 |
| 8B | n-octyl | pyridine/ R' = n-heptyl X = Cl | IV, R' = n-heptyl | 86 |
| 9 | n-octyl | pyridine/ R' = 1-ethyl-pentyl X = Cl | IV, R' = 1-ethyl-pentyl | 85 |
| 10 | n-octyl | pyridine/ R' = methyl X = Cl | IV, R' = methyl | 89 |
| 11 | n-octyl | pyridine | IV, R' = phenyl | 91 |

Certain compounds having structures IV and V were tested in PVC applications. For instance, the amidodi ester IV of iminodiacid acid in which R' was n-octyl and R' was n-heptyl were found to act as a PVC plasticizer equivalent to dioctylphtalate. Equally acted also the N-acetylated derivative of di(2-ethylhexyl)ester (IV in which R was 2-ethylhexyl and R' was methyl) and the N-benzoylated derivative of di(2-ethylhexyl)ester (IV in which R was 2-ethylhexyl and R' was phenyl).

The compounds in which R was an alkyl and R' was H, alkyl or phenyl were found to exert a synergetic effect when they were used together with Cd/Zn stabiliser. This fact is seen in VDE values gathered in Table 2, indicating the thermal stability (thermal stability values are defined according to VDE standard 0209 (3.69).

TABLE 2

| Test | PVC | DOP | $A^1$ | $B^1$ | $C^1$ | $D^1$ | $E^1$ | Stab. value, min. | VDE 2 |
|---|---|---|---|---|---|---|---|---|---|
| 1 | 100 | 50 | | | | | | — | |
| 2 | 100 | 50 | | | | | | 5 | 2 |
| 3 | 100 | 45 | 5 | | | | | — | |
| 4 | 100 | 45 | 5 | | | | | 0,6 | 8 |
| 5 | 100 | 45 | | 5 | | | | 0,6 | 6 |
| 6 | 100 | | | | 50 | | | 0,6 | 5 |
| 7 | 100 | | | | | 50 | | 0,6 | 5 |
| 8 | 100 | | | | | | 50 | 0,6 | 6 |

$^1$A = III in which R was 2-ethylhexyl and R' was H
B = III + IV (1:1) in which R was 2-ethylhexyl and R' was H or 1-ethylpentyl
C = IV in which R was n-octyl and R' was 1-heptyl
D = IV in which R was 2-ethylhexyl and R' was 1-methyl
E = IV in which R was 2-ethylhexyl and R' was phenyl.

We claim:
1. Derivatives of N,N-bis(2-2-dimethyl-2-carboxyethyl)amine, characterized in that their formula is as follows:

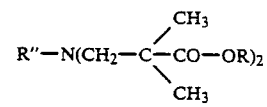

in which R is a $C_1$-$C_{10}$-alkyl- or aryl group, and R" is $C_3$-$C_{12}$-alkyl or aryl group with or without an ester group in the carbon chain.

2. A manufacturing process for preparing the compounds according to claim 1, comprising a condensation reaction between ammonium halide or sulphase, formaldehyde and isobutyraldehyde are made to react with one another according to formula (3):

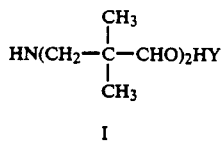

wherein y is a halide or sulphate group, the product obtained from the above condensation reaction being oxidized according to formula (4)

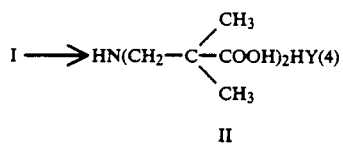

the compound II obtained in acid form, said compound II thereafter being esterified with alcohol according to formula (5):

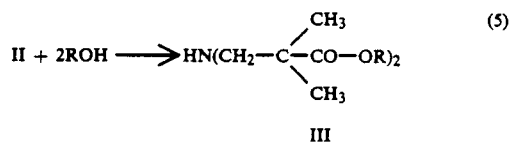

and the compound III thus obtained being alkylated with alkyl halide or arylated with an aryl halide according to formula (7):

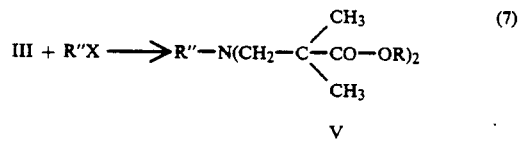

in which reaction formula R is a $C_1$-$C_{10}$- alkyl or aryl group, and R" is a $C_3$-$C_{12}$-alkyl or aryl group which may contain an ester group in the carbon chain, and X is a halide group.

3. Procedure according to claim 2, characterized in that in the condensation reaction according to formula (3) paraformaldehyde, trioxane or about 40% of the aqueous solution of formaldehyde is used as a formaldehyde source.

4. Procedure according to claim 3, characterized in that the condensation reaction according to formula (3) carried out at 50 to 90° C. under refluxing conditions or under small over-pressure.

5. Procedure according to claim 3, characterized in that the oxidation reaction (4) was carried out at 50 to 75° C. with peroxide.

6. Procedure according to claim 3, characterized in that the esterification reaction is performed at 100 to 150° C. using gaseous hydrochloric acid as the catalyst.

7. Procedure according to claim 3 characterized in that the acylation reaction (6) is accomplished with acid chloride at 20 to 100° C.

8. Procedure according to claim 3, characterized in that the alkylation reaction (7) is performed with the ester of 2-chloroacetic acid at 140 to 150° C.

9. A plasticizer comprising an effective amount of one or more of the compounds according to claim 1.

10. A stabilizing agent for polymers comprising an effective amount of one or more of the compounds according to claim 1.

11. A lubricant comprising an effective amount of one or more of the compounds according to claim 1.

12. An emulgator comprising an effective amount of one or more of the compounds according to claim 1.

13. An anticorrosive agent comprising an effective amount of one or more of the compounds according to claim 1.

14. A metal complexing agent comprising an effective amount of one or more of the compounds according to claim 1.

* * * * *